United States Patent [19]

Amrhein et al.

[11] Patent Number: 5,016,472
[45] Date of Patent: May 21, 1991

[54] DUSTY ENVIRONMENT WET BULB INDICATOR

[75] Inventors: Gerald T. Amrhein, Louisville; Paul S. Nolan, North Canton, both of Ohio

[73] Assignee: The Babcock & Wilcox Company, New Orleans, La.

[21] Appl. No.: 491,139

[22] Filed: Mar. 9, 1990

[51] Int. Cl.⁵ .............................................. G01N 25/64
[52] U.S. Cl. ..................................... 73/338; 73/29.02
[58] Field of Search ........... 73/73, 29.02, 338, 338.06; 374/39

[56] References Cited

U.S. PATENT DOCUMENTS

| | | | |
|---|---|---|---|
| 3,603,135 | 9/1971 | Kawaguchi | 73/29.02 |
| 3,934,454 | 1/1976 | Simo | 73/29.02 |
| 4,175,436 | 11/1979 | Crawford et al. | 73/338.6 |
| 4,222,261 | 9/1980 | Leblanc et al. | 73/29 |
| 4,409,834 | 10/1983 | Kethley | 73/336 |
| 4,412,647 | 11/1983 | Lampert | 374/39 |
| 4,461,167 | 7/1984 | Kent et al. | 73/29.02 |
| 4,559,823 | 12/1985 | Rosen et al. | 73/338 |
| 4,625,550 | 12/1986 | Sorensen | 73/338 |
| 4,856,352 | 8/1989 | Daum et al. | 73/864.73 |

Primary Examiner—Daniel M. Yasich
Attorney, Agent, or Firm—Vytas R. Matas; Robert J. Edwards; Daniel S. Kalka

[57] ABSTRACT

An apparatus and method for measuring the wet and dry bulb temperatures of a hot flue gas stream containing fly ash and particulates by providing a sample sheath (12) in a gas duct (10) with a dry bulb sensor (16) and a wet bulb sensor (18) located within the sample sheath (12). The sample sheath (12) includes a self-cleaning dust filter (14) which removes the ash and particulates from the flue gas stream and a self-regulating water reservoir (26, 28) to continuously supply water for the wet bulb sensor (18).

7 Claims, 1 Drawing Sheet

DUSTY ENVIRONMENT WET BULB INDICATOR

BACKGROUND OF THE INVENTION

1. Field of the Invention

The present invention relates in general to measuring the humidity of a gas stream, and in particular, is directed to measuring the wet and dry bulb temperatures of a gas stream from a fossil fuel combustion process containing fly ash and other particulate matter.

2. Description of the Related Art

A psychrometer is a common device that measures the water content of air by simultaneously measuring the wet and dry bulb temperature. These values are used with a psychrometric chart to determine relative humidity.

There are numerous forms of psychrometers known in the prior art such as are disclosed in U.S. Pat. Nos. 4,175,436; 4,461,167; 4,222,261; 4,559,823; 4,625,550; and 4,409,834. There are also several commercial devices currently available for measuring the wet and dry bulb temperature of air. One such commercial device is the Assman psychrometer. This device uses a small blower to draw air across a pair of matched thermocouples of which one is wrapped with a saturated wick.

In the standard sling psychrometer, there are two thermometers, one for the wet bulb and one for the dry bulb. The wet bulb thermometer is wrapped with a porous material or wick and soaked in water. When it is whirled in air, evaporation from the wick causes the wet bulb thermometer to cool. At a steady state, the temperature with the wet bulb thermometer is known as a wet bulb temperature. For air/water systems, the wet bulb temperature is equal to the adiabatic saturation temperature. For combustion gases, these parameters differ by a few degrees.

While the foregoing devices function well for air/water systems, they are not suitable for a gas stream from a fossil fuel combustion process such as a coal combustion process. The flue gas contains fly ash and other particulates which would deposit onto and contaminate the wetted wick- causing incorrect measurements.

It is important to closely control and monitor flue gas humidity due to the recent interest in clean coal technology. Most of the current emission control technologies incorporate dry scrubbing or in-duct injection of an alkali based sorbent followed by flue gas humidification. Humidification increases overall sulfur oxide removal and further enhances particulate removal with an electrostatic precipitator. Consequently, it is necessary to operate a humidifier at a very low approach to adiabatic saturation temperature ($T_{as}$). As a result, the likelihood of system failure increases from incomplete evaporation within the duct.

To avoid this type of failure, it is imperative that the amount of fluid injection be closely controlled and monitored. Fluid injection is controllable by a measurement of the degree of humidification of the treated gas. The instruments presently available for monitoring humidity of a flue gas employ expensive, sensitive optical and electronic sensors. These instruments are complicated and require periodic maintenance and calibration by skilled technicians.

Thus there is a need for an inexpensive, simple and low maintenance device for measuring the humidity of a dusty flue gas stream. The device needs to be constructed of materials that can withstand temperatures up to 400° F. and is not sensitive to vibrations, weather, or corrosion. The device needs to make measurements which are primary measurements so as not to require calibration. The device must be constructed of readily available and inexpensive commercial equipment so as to facilitate repairs and construction.

SUMMARY OF THE INVENTION

The present invention solves the aforementioned problems by providing an apparatus and method for measuring the humidity of a flue gas stream. Advantageously, the apparatus of the present invention comprises a sample sheath which extends into the flue gas duct. The sample sheath has a self-cleaning filter for separating the particulate matter from the sampled flue gas. Two sensors are positioned within the sample sheath for measuring the wet and dry bulb temperature of the gas. The second sensor is provided with a self-regulating water reservoir to provide a continual supply of water to the wick surrounding the sensor. The apparatus is further provided with means for drawing the flue gas into the sample sheath for sampling.

Accordingly, one aspect of the present invention is directed to a method and apparatus for accurately measuring the humidity of a flue gas stream containing fly ash and particulate matter.

Another aspect of the present invention is to provide an inexpensive, simple, and low maintenance device capable of withstanding temperatures up to 400° F.

A further aspect of the present invention is to provide a device that is not sensitive to vibrations, weather or corrosion.

The various features of novelty characterized in the present invention are pointed out with particularity in the claims annexed to and forming a part of this disclosure. For a better understanding of the invention and the operating advantages attained by its use, reference is made to the accompanying drawings and descriptive matter in which the preferred embodiment of the invention is described.

DESCRIPTION OF THE PREFERRED EMBODIMENT

Figure 1:
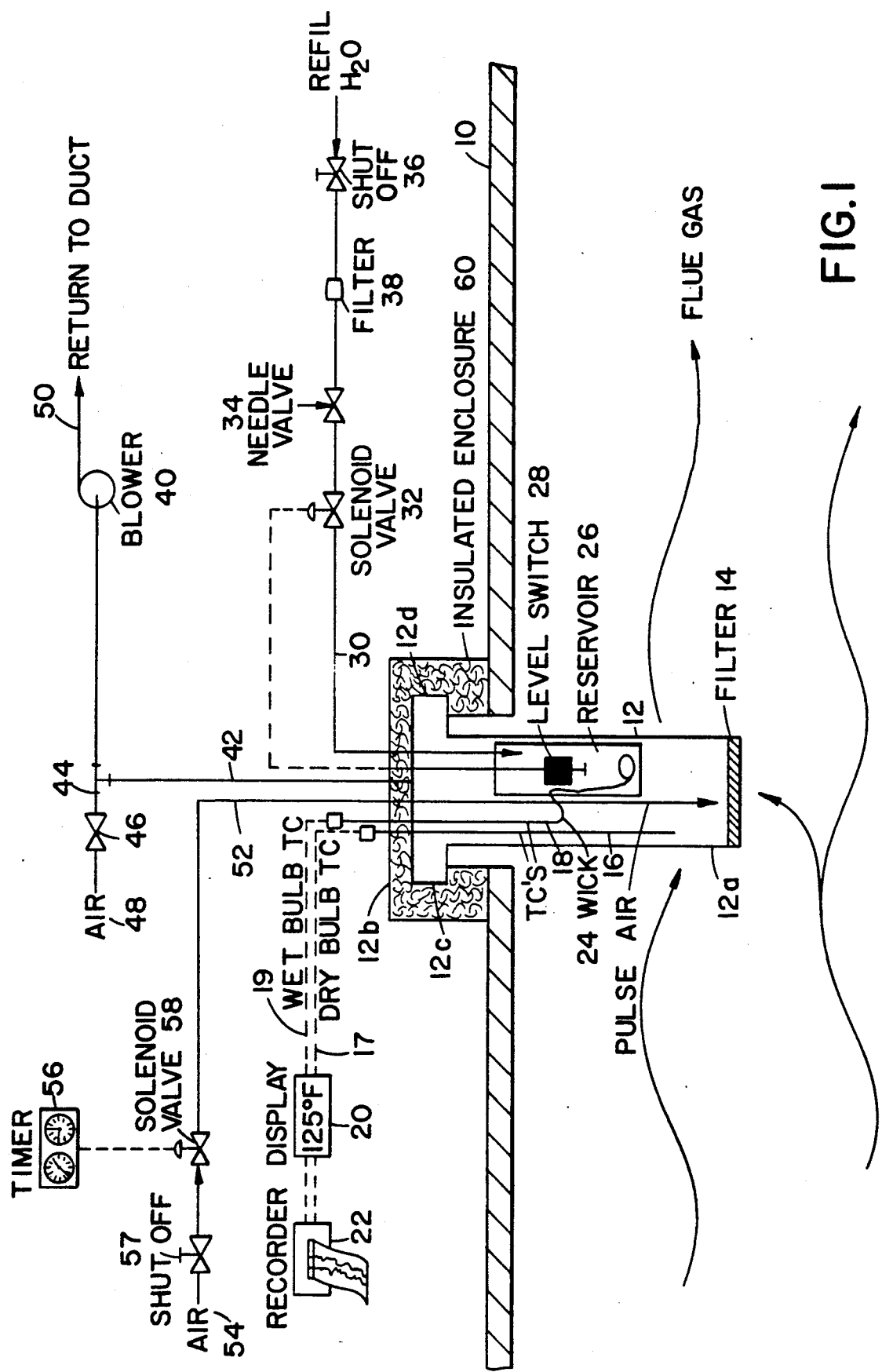
FIG. 1 is a schematic sectional illustration of the present invention in position in a flue gas duct.

In FIG. 1, the flue gas emitted from a fossil fuel combustion process flows in the direction of the arrows in a flue gas duct (10). Situated in duct (10) is a sample sheath (12) which extends into the duct (10). It is Preferred that sample sheath (12) be cylindrical and constructed of stainless steel such as a pipe, but it is envisionable that other forms of a sample sheath are equally suitable. Sample sheath (12) has a filter (14) positioned at the opening of the end (12a) situated in the duct (10). Sample sheath (12) extends to a predetermined depth into duct (10) to ensure representative sampling of the flue gas stream. Preferably, the sample sheath (12) extends in a direction normal to the duct (10). The orientation of the filter (14) with respect to the direction of the flue gas flow is not critical. Filter (14) is preferably situated at an angle opposite the flow so that the sample sheath (12) assists in the separation of the fly ash and other particulates. The other end (12b) of sample sheath (12) is secured by flanges (12c, 12d) or any suitable fastening means like a threaded connection to hold the sample sheath (12) in position in duct (10).

Inside sample sheath (12) there are two sensors, for example thermocouples (16, 18). The first thermocouple (16) measures the dry bulb temperature and can be connected to a display (20) and recorder (22) by line (17). The second thermocouple (18) has a wick (24) substantially surrounding it. Wick (24) provides water to cause thermocouple (18) to register the wet bulb temperature at steady state. The second thermocouple (18) can be connected to display (20) and recorder (22) by line (19).

A portion of the wick (24) is immersed in reservoir (26) which supplies the water. The wick (24) draws the water from the reservoir (26) to cool thermocouple (18). The reservoir (26) is located within sample sheath (12) and has a level switch (28) which regulates the level of the water to provide a continuous source to the wick (24). Supply line (30) provides the water to the reservoir (26). A solenoid valve (32) is situated within the supply line (30) and is responsive to the level switch (28) for controlling the amount of water supplied. Additional valves (34, 36) may be added to the supply line (30) for optimum control of flow and pressure of the water. A filter 38) cleans the water so as to avoid contaminating the wick (24).

A blower (40) or a vacuum pump provides means for drawing the flue gas into the sample sheath (12) by means of a pipe or conduit (42). Blower (40) draws the sample flue gas through filter (14) into the sample sheath (12) for sampling. A tee (T) connection (44) in pipe (42) along with a valve (46) controls the sampling rate by allowing ambient air from a source (48) into the duct (10) downstream of the measurement location. The sampled gas may be returned to the duct (10) through pipe (50) after sampling.

Periodically, the solids that deposit on the filter (14) are removed with pulses of a high pressure fluid such as air. Line (52) which is supplied with air from source (54) extends into the sample sheath (12) and directs the air at the filter (14) to remove fly ash and other particulates. An adjustable timer (56) controls a solenoid valve (58) in the air line (52) for regulating the pulse frequency and duration. The pulse frequency may range from 0–3 hours with the pulse duration lasting from 0–15 seconds. An additional shut-off valve (57) may be inserted prior to valve (58). In the above manner, the filter (14) is periodically cleaned at predetermined intervals from the fly ash and other particulates in the flue gas stream.

All of the lines and connections of the present invention enter the sample sheath end (12b). Insulated enclosure (60) seals end (12b) and prevents the ingress of ambient air.

The apparatus of the present invention is constructed of standard stainless steel materials and fittings to prevent corrosion while facilitating repairs. It is envisionable depending upon the particular application that other materials may be suitable.

The present invention finds particular utility due to the recent interest in emission control technology. As stated earlier most flue gas desulfurization systems inject an alkali-based sorbent in the duct with some type of humidification to increase the overall sulfur oxides removal while enhancing the particulate collector's performance. To achieve maximum sulfur oxide removal with alkali utilization, it is necessary to operate the humidifier at a very low approach to saturation temperature. However, this increases the likelihood of system failure due to incomplete evaporation within the duct. As a result, it is necessary to closely control and monitor the amount of fluid injection which is controllable by a measurement of the degree of humidification of the treated flue gas.

Advantageously, a computer (not shown) may be connected to the first and second sensors (16, 18) which then can be used to control the flue gas humidification or slurry injection system.

The present invention may also find utility in industry employing spray drying to concentrate or create a product such as in food processing and domestic products.

While a specific embodiment of the invention has been shown and described in detail to illustrate the application and principles of the invention, certain modifications and improvements will occur to those skilled in the art upon reading the foregoing description. It is thus understood that all such modifications and improvements have been deleted herein for the sake of conciseness and readability but are properly in the scope of the following claims. Several examples of such modifications would be to include different level switches, more elaborate filter systems, a reservoir permitting horizontal installation, or a microprocessor to calculate and display humidity.

We claim:

1. An apparatus for measuring wet and dry bulb temperatures of a flue gas stream flowing in a duct, comprising;
   a sample sheath extending into the gas duct with one end of said sample sheath being secured to the duct and the opposite end of said sample sheath having a filter within the gas duct;
   a first sensor for measuring a dry bulb temperature of the flue gas situated in said sample sheath;
   a second sensor for measuring a wet bulb temperature of the flue gas situated in said sample sheath;
   a wick surrounding said second sensor;
   a reservoir located within said sample sheath for providing water to said wick which is partly immersed in said reservoir, said reservoir being connected to a water supply line;
   a level switch for regulating an amount of water in said reservoir, said level switch activating a valve on the water supply line; and
   means for drawing the flue gas into the sample sheath.

2. An apparatus as recited in claim 1, further comprising means for displaying the sensor signals.

3. An apparatus as recited in claim 1, further comprising means 52, 56, 58, etc. for cleaning the sample sheath filter.

4. An apparatus as recited in claim 3, wherein said cleaning means includes a source of fluid under high pressure being directed at said filter, said fluid being in communication with a timer for regulating frequency and duration of the high pressure fluid.

5. An apparatus as recited in claim 1, wherein said drawing means includes a blower with a valve arrangement for sampling the flue gas and returning the sample to the duct after sampling.

6. An apparatus as recited in claim 1, further comprising a filter connected in the fluid supply line for cleaning the fluid prior to the reservoir.

7. A method for measuring wet and dry bulb temperatures of a gas stream, comprising the steps of:
   positioning a sample sheath into a gas duct with one end of the sample sheath being secured to the duct with the opposite end having a filter inside the gas duct;
providing a first and second sensor inside the sample sheath, the first sensor being employed for measuring the dry bulb temperature;
surrounding the second sensor with a wick partially immersed in a reservoir connected to a water supply line;
supplying a continuous amount of water to said wick to allow the second sensor to measure the wet bulb temperature;
drawing the flue gas into the sample sheath through the filter for sampling the flue gas stream; and
cleaning the filter in the sample sheath at predetermined intervals with a high-pressure field.

* * * * *